United States Patent
Benzel et al.

(10) Patent No.: US 6,832,523 B2
(45) Date of Patent: Dec. 21, 2004

(54) MICROMECHANICAL COMPONENT AND MANUFACTURING METHOD

(75) Inventors: Hubert Benzel, Pliezhausen (DE); Heribert Weber, Nuertingen (DE); Frank Schaefer, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 29 days.

(21) Appl. No.: 10/017,772

(22) Filed: Oct. 29, 2001

(65) Prior Publication Data

US 2002/0139171 A1 Oct. 3, 2002

(30) Foreign Application Priority Data

Oct. 27, 2000 (DE) .......................................... 100 53 326

(51) Int. Cl.[7] .............................................. G01L 1/00
(52) U.S. Cl. .......................................... 73/763; 73/723
(58) Field of Search .......................... 73/29.01, 514.52, 73/723; 257/467

(56) References Cited

U.S. PATENT DOCUMENTS 5,714,791 A * 2/1998 Chi et al. ................... 257/467
5,852,245 A * 12/1998 Wesling et al. ................ 73/723
6,076,404 A * 6/2000 Muchow et al. .......... 73/514.32

FOREIGN PATENT DOCUMENTS

| WO | WO 96 05506 | | 2/1996 |
| WO | WO 03 012420 | * | 7/2001 |

OTHER PUBLICATIONS

D. Heinze, *Semiconductor Technologies for Manfuctring Modern Moisture Sensors*, Sensor 91. Nuremberg 1991, Kongreβband (Convention Volume) IV, 112–121).

Lammel et al., *Free-standing Mobile 3D Microstructures of Porous Silicon*, Proceedings of the 13th European Conference on Solid–State Transducers, Eurosensors XIII, The Hague, 1999, 535–536.

\* cited by examiner

Primary Examiner—Edward Lefkowitz
Assistant Examiner—Andre Allen
(74) Attorney, Agent, or Firm—Kenyon & Kenyon

(57) ABSTRACT

A micromechanical component having a substrate and a diaphragm positioned on the substrate. Underneath the diaphragm a region made of porous material is provided, which mechanically supports the diaphragm and thermally insulates it.

29 Claims, 5 Drawing Sheets

US 6,832,523 B2

MICROMECHANICAL COMPONENT AND MANUFACTURING METHOD

FIELD OF THE INVENTION

The present invention relates to a micromechanical component having a substrate and a diaphragm positioned on the substrate, and to a corresponding manufacturing method.

BACKGROUND INFORMATION

Even though it may be applied to any number of micromechanical components and structures, particularly sensors and actuators, the present invention as well as the problem it is based on are explained with reference to a micromechanical dew point sensor which can be manufactured within the technology of silicon surface micromechanics.

Already published in PCT Publication No. 96/05506 is the principle of sensing the dew point by cooling a micromechanical sensor element by a Peltier element until moisture condenses on the surface. The temperature of the sensor element at which condensation begins is measured using a temperature sensor, thereby determining the dew point.

In particular, PCT Publication No. 96/05506 describes a device including a Peltier element, a temperature sensor, an interdigital capacitor and a microprocessor for evaluation. The beginning of dew formation can be determined by changing the capacitance of the interdigital capacitor.

A further possibility is to determine dew formation by an optical measurement (also see D. Heinze, "Semiconductor Technologies for Manufacturing Modern Moisture Sensors", Sensor 91, Nuremberg 1991, Kongreßband (Convention Volume) IV, 112–121).

The manufacture of a Peltier element using—and p-doped semiconductors connected by a metal bridge has long been known (see, for example, M. von Ardenne et al., "Effekte der Physik und ihre Anwendungen" (The Effects of Physics and their Applications), Publishing House Harri Deutsch, Frankfurt on Main 1990, page 399).

U.S. Pat. No. 5,714,791 describes a Peltier element by way of—and p-doped semiconductor areas on a diaphragm, the diaphragm being thermally insulated by etching a cavity from the reverse side of the substrate.

The method of etching silicon porous ("anodizing") is a part of the related art and is described in numerous publications. The method of producing a cavity under porous silicon has likewise been published (G. Lammel, P. Renaud, "Free-standing Mobile 3D Microstructures of Porous Silicon", Proceedings of the 13th European Conference on Solid-State Transducers, Eurosensors XIII, The Hague, 1999, 535–536).

With regard to the known dew point sensors, the disadvantageous fact has become apparent that their manufacture is difficult and costly.

SUMMARY OF THE INVENTION

The micromechanical component according to the present invention and the corresponding manufacturing method, respectively, have the advantage that simple and cost-effective manufacture of a component is possible, having a thermally decoupled diaphragm area.

For example, by using porous silicon, a deep cavity having a diaphragm lying above it can be manufactured relatively simply. Furthermore, there is the possibility of making a defined region on a wafer porous up to a defined thickness, and, as an option, of oxidizing to a higher valency in order to create a stable framework having low thermal conductivity. When producing a dew point sensor using this method, the following further advantages are available:

low power consumption because of good thermal decoupling integration of a sensor element, e.g. a Peltier element, on the chip possible integration of a circuit on the sensor element very small size low response time because of the small mass that has to be retempered The idea at the basis of the present invention is that, underneath the diaphragm, a region of porous material supporting the diaphragm and thermally insulating it is provided.

According to a preferred further development, the porous material is formed from the substrate material. This is particularly well possible in the case of a silicon substrate.

According to a further preferred development, a hollow space is formed underneath the region made of porous material.

As in still another preferred further development, the diaphragm layer is formed by oxidizing the substrate surface and the surface of the porous region. Thereby the deposition of an additional diaphragm layer can be dispensed with.

According to a further preferred development, the region made of porous material is completely oxidized. Such an oxidation is easily possible based on the porous structure, and raises the thermal insulating capability.

According a further preferred refinement, the component has a dew point sensor in turn including a thermocouple for measuring the temperature, provided above the region made of porous material; an interdigital capacitor provided above the region made of porous material; a Peltier element device having one or a plurality of Peltier elements for heating and cooling the diaphragm; and a dew point measuring device for measuring the dew point with the aid of the capacitance of the interdigital capacitor and the temperature measured by the thermocouple.

In another further preferred development the component has a heat radiation sensor, which further includes an absorption device, provided above the region made of porous material, for absorbing heat radiation; a Peltier element device having one or a plurality of Peltier elements for creating a thermoelectric voltage corresponding to a temperature difference between a diaphragm region next to the region made of porous material and a diaphragm region above the region made of porous material; and a temperature measuring device for measuring the temperature in the diaphragm region above the region made of porous material.

In still another preferred development the temperature measuring device measures the temperature based on the thermoelectric voltage.

And in yet another further preferred development, a control device is provided for controlling the temperature in the diaphragm region above the region made of porous material, using the Peltier element device, and the temperature measuring device measures the temperature based on the regulated output.

DETAILED DESCRIPTION

Figure 1:
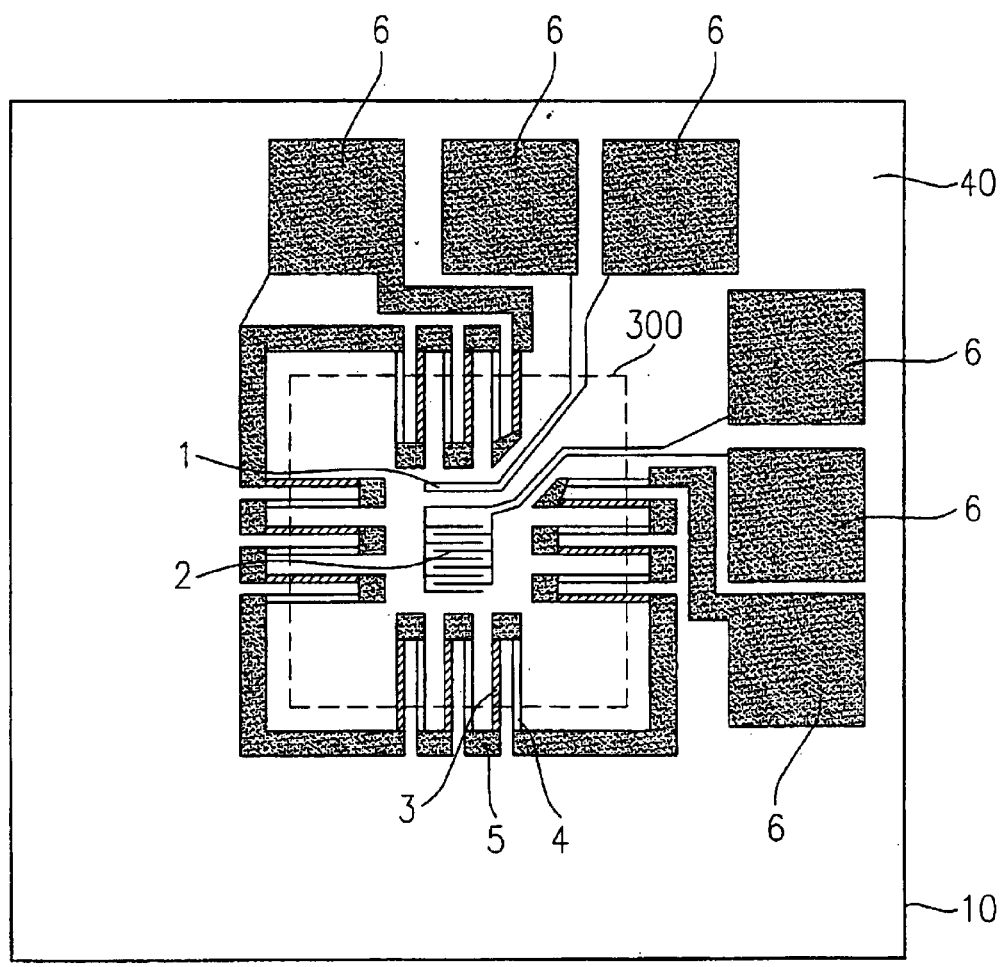
FIG. 1 shows a top view of a dew point sensor according to a first specific embodiment of the present invention.

In the figures, the same reference numerals denote the same or functionally the same component parts.

FIG. 1 shows a top view of a dew point sensor according to a first specific embodiment of the present invention.

In FIG. 1, reference numeral 1 denotes a thermocouple, numeral 2 denotes an interdigital capacitor, 3 a p-doped printed circuit trace, 4 an n-doped printed circuit trace, 5 a metal wire, 6 a contact surface and contact pads, respectively, 10 a semiconductor substrate, 40 a diaphragm layer positioned on the surface of the semiconductor substrate, and 300 the borderline of a region in which a region made of porous material is provided underneath diaphragm layer 40, and supporting diaphragm layer 40 mechanically and insulating it thermally. In the present case the substrate material is silicon and the porous material is anodized (porously etched) silicon.

For the operation of the sensor structure shown in FIG. 1, the Peltier element device formed from the various Peltier elements 3, 4, 5 connected in series is regulated in such a way that, on the surface of diaphragm layer 40, within region 300, the transition from the bedewed to the non-bedewed condition, or vice versa, can be determined by cooling or heating, since this region is thermally insulated from the environment. During this transition, the capacitance of interdigital capacitor 2 on diaphragm layer 40 changes because of the high dielectric constant of water ($\epsilon_r=81$). The corresponding dew point temperature is then measured using thermocouple 1.

Figure 2:
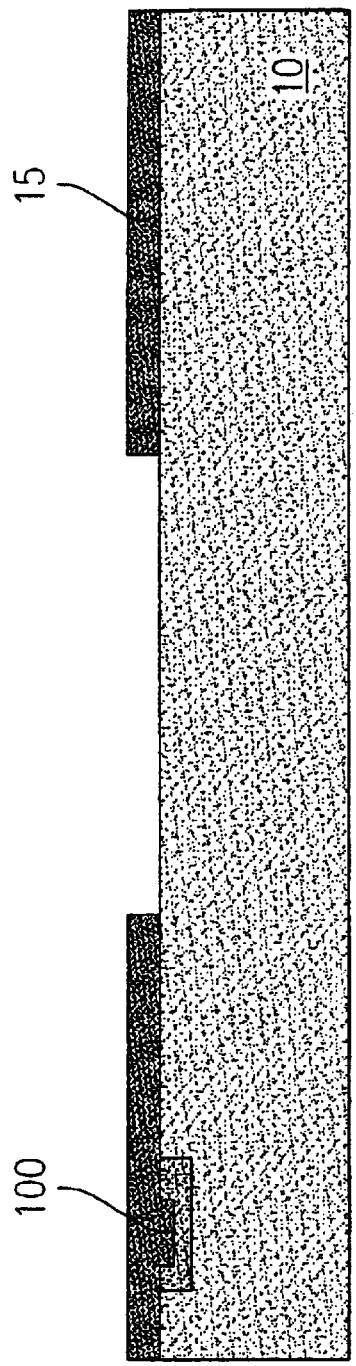
FIG. 2 shows a first manufacturing step for manufacturing the dew point sensor in FIG. 1.
Figure 3:
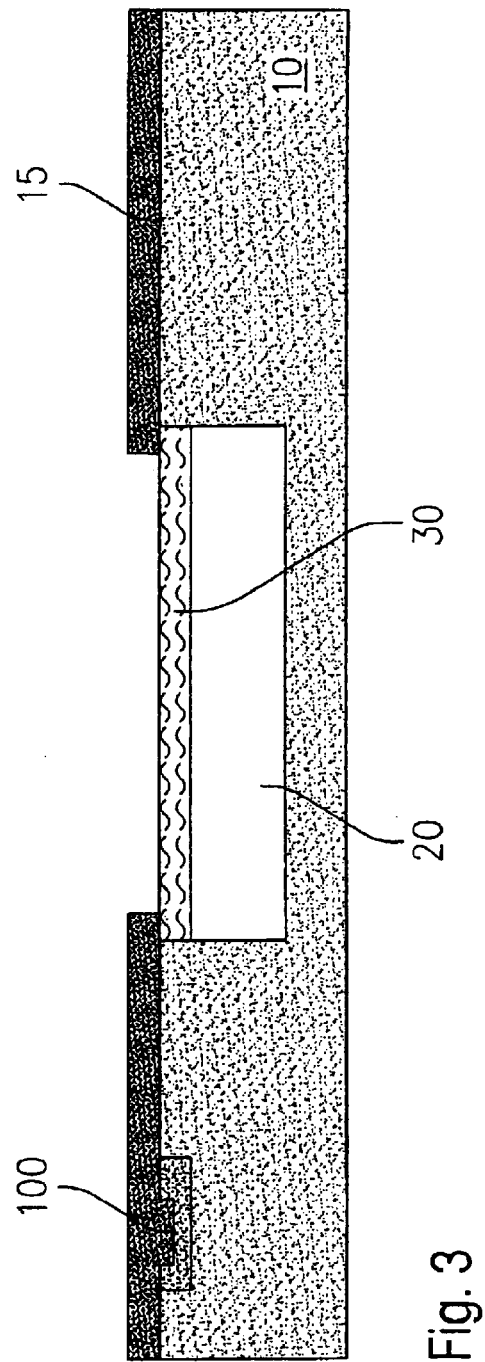
FIG. 3 shows a second manufacturing step for manufacturing the dew point sensor in FIG. 1.
Figure 4:
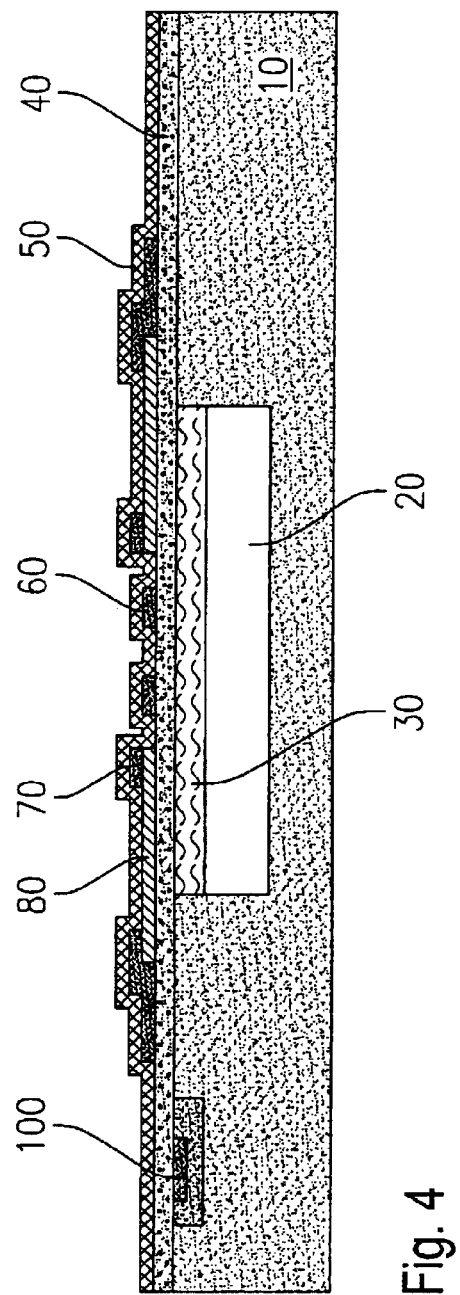
FIG. 4 shows a third manufacturing step for manufacturing the dew point sensor in FIG. 1.

FIGS. 2–4 show manufacturing steps for manufacturing the dew point sensor in FIG. 1.

In FIG. 2, in addition to the reference numerals already introduced, 15 denotes a mask, such as a resist mask, and 100 denotes circuit components of a sensor circuit that is not explained more closely. Substrate 10 shown in FIG. 2 is a silicon substrate. Other substrates can, of course, also be used, such as a substrate having an epitaxy layer. However, for simplicity's sake, in the following, a wafer substrate is assumed.

According to FIG. 3, using the known method of porous etching, a structure is generated in which the substrate material is made porous in a certain region 30 and subsequently a hollow space 20 is formed underneath porous region 30, that is, a part of porous region 30 is removed, which leads to the structure shown in FIG. 3.

In FIG. 4, reference numeral 40 denotes the diaphragm layer, 50 an insulating layer, 60 a measuring capacitance, 70 a metal printed circuit trace and 80 Peltier printed circuit traces corresponding to printed circuit traces 3, 4 in FIG. 1.

In order to manufacture the structure shown in FIG. 4, after removing mask 15, the porous area 30 is closed by depositing diaphragm layer 40, which is made, for example, of nitride, oxide or polysilicon. A further possibility of forming diaphragm layer 40 is oxidizing the substrate surface and the surface of porous area 30.

In this case, this airtight closing of hollow space 20 does not absolutely have to take place after producing the hollow space 20, but can be carried out as one of the last process steps. The latter has the advantage that, during processing, diaphragm layer 40 does not bulge out and thus lead to image defects during a structuring process. The internal pressure ultimately forming in hollow space 20 depends on the pressure conditions prevailing at the deposition or oxidation, respectively. Measuring capacitance 60 with respect to interdigital capacitor 2 in FIG. 1, the metal printed circuit traces 70 and the Peltier printed circuit traces 80 are produced on diaphragm layer 40. Further functional layers can be put down and structured between diaphragm layer 40 and printed circuit traces 70 and above the printed circuit traces, respectively.

The present specific embodiment has a hollow space 40 having a closed-in vacuum under diaphragm layer 40, in order to guarantee good thermal insulation from substrate 10. Thus, insulating layer 50 protects the formed structure from environmental influences.

Figure 5:
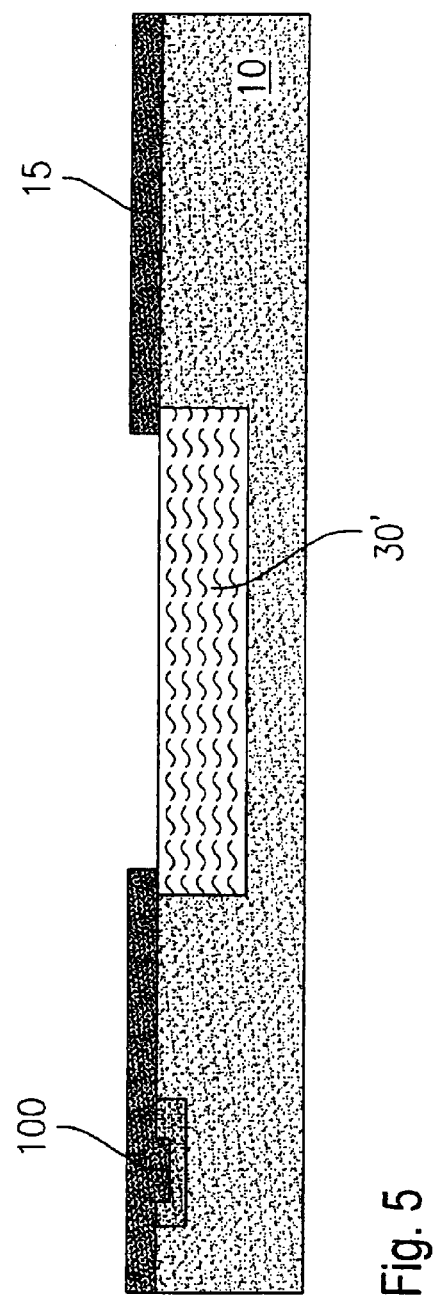
FIG. 5 shows a first manufacturing step for manufacturing the dew point sensor according to a second specific embodiment of the present invention.
Figure 6:
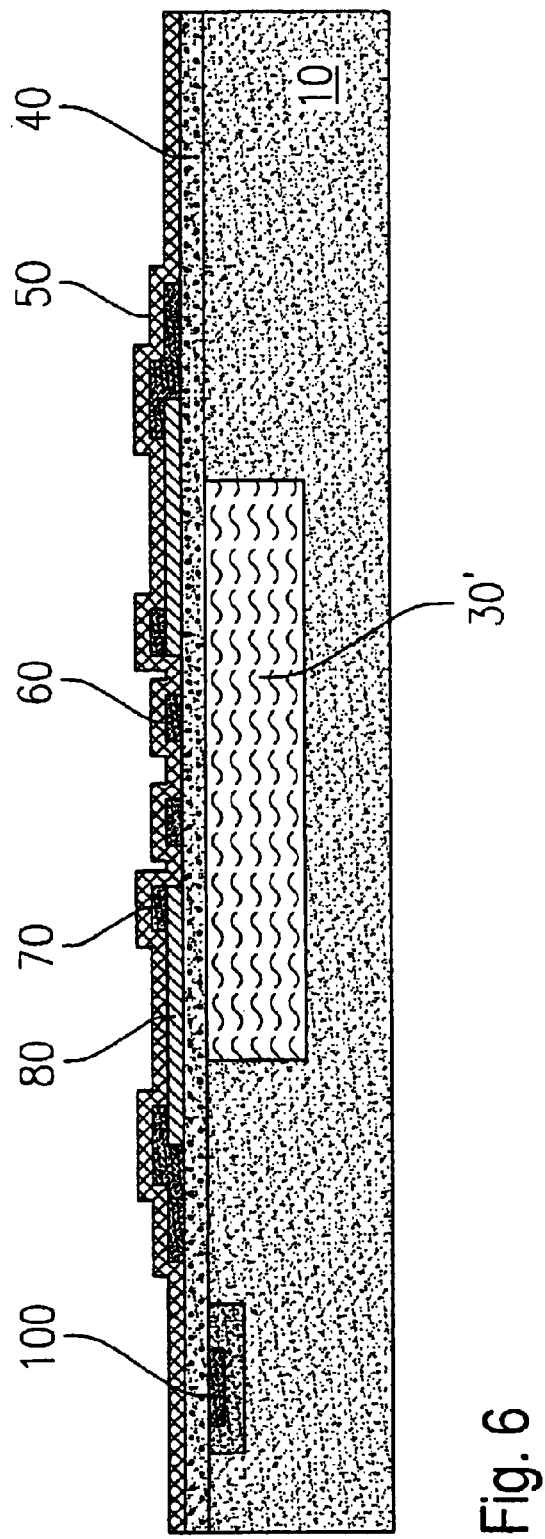
FIG. 6 shows a second manufacturing step for manufacturing the dew point sensor according to the second specific embodiment of the present invention.

FIGS. 5–6 represent manufacturing steps for producing the dew point sensor according to a second specific embodiment of the present invention.

In the case of the second specific embodiment shown with reference to FIGS. 5 and 6, no hollow space is formed under the substrate area 30' made porous, but after removing mask 15 porous area 30' is closed directly by depositing diaphragm layer 40 or by oxidation, respectively.

Here, oxidation (not shown) has the advantage that the oxide has a lower thermal conductivity than silicon, whereby better decoupling from substrate 10 can be guaranteed. Just as with the first specific embodiment, the printed circuit traces etc are produced on diaphragm layer 40.

Figure 7:
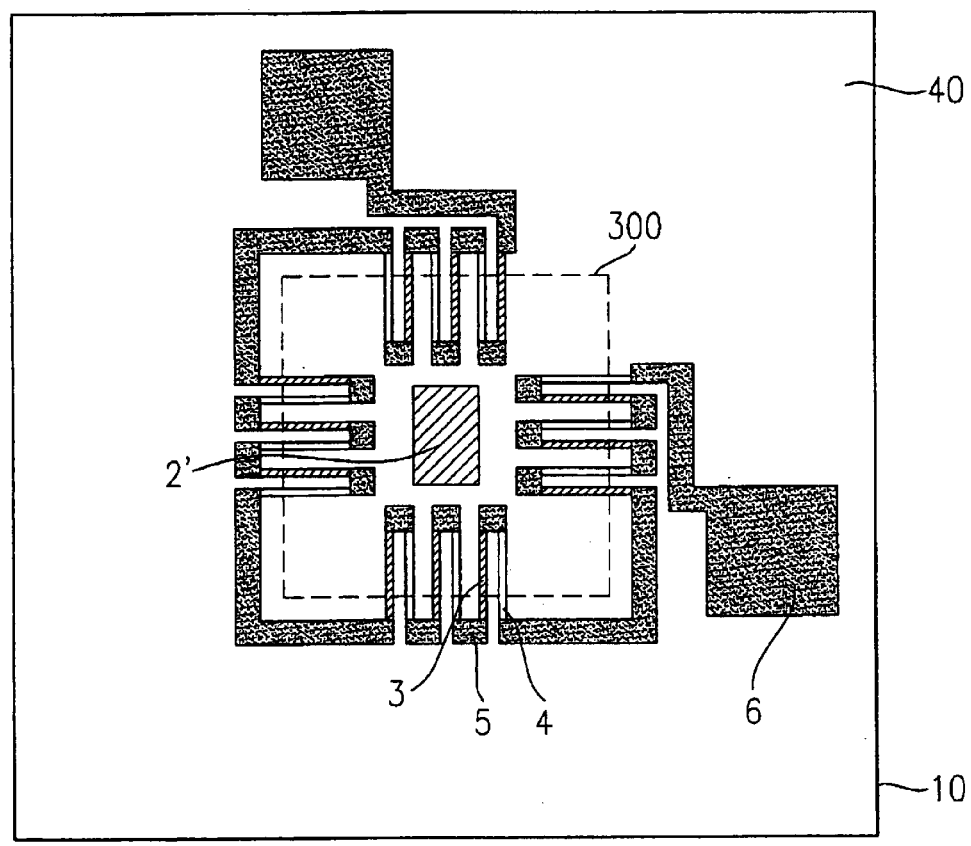
FIG. 7 shows a top view of a heat radiation sensor according to a third specific embodiment of the present invention.

FIG. 7 is a top view of a heat radiation sensor according to a third specific embodiment of the present invention.

In the specific embodiment shown in FIG. 7, in the place of thermocouple 1 and interdigital capacitor 2, a heat radiation sensor device 2' is provided on the middle diaphragm region, which absorbs incident infrared radiation and converts it to heat. Thus a heat radiation sensor can be produced in a simple manner. The temperature difference between the middle region of diaphragm 40 and the surrounding region leads to a thermoelectric voltage at Peltier elements 3, 4, 5, which now function as thermocouples. Thus, the thermoelectric voltage is a measure of the absorbed infrared radiation.

In a further specific embodiment (not shown) it is possible to regulate the middle region of the diaphragm in such a way that its temperature remains the same as that of a thermocouple provided upon it, while the heat generated by the infrared radiation is dissipated by the Peltier element. Thus, the cooling capacity of the Peltier element is a measure of the absorbed infrared radiation.

Although the present invention is described based on the aforementioned preferred exemplary embodiments, the method is not limited thereto, but can be modified in a plurality of ways.

In the above examples, the dew point sensor and heat radiation sensor, respectively, according to the present invention, have been specified in a simple form for the purpose of explaining their basic principles. Combinations of the examples and substantially more complicated refinements using the same basic principles are, of course, conceivable.

It is further possible, after or between the above process steps, to etch selectively the porous region 30, 30'. For this purpose, one or a plurality of openings can be produced in diaphragm layer 40, through which a selectively acting etching medium, in a fluid or gaseous state, can dissolve out the porous region partially or completely. Subsequently the openings can be closed again, a vacuum being preferably enclosed in hollow space 20 during this, to guarantee optimal thermal decoupling of diaphragm 40 from substrate 10. The openings can also deliberately not be closed Thereby the middle diaphragm region can be so configured with functional elements that it is then connected by only a few links to the substrate outside the cavity (e.g. connection by only two links in the form of a bridge). This leads to very good lateral thermal decoupling, which is important for the functioning of the Peltier element.

It is possible to produce the measuring capacitor above the Peltier element, an insulating layer being inserted between the two layers.

Furthermore, the Peltier printed circuit traces can be produced from polysilicon on an insulating closing layer.

It is further possible to produce the Peltier printed circuit traces as p-doped and n-doped regions in an epitaxy layer which is used as a closing layer.

It is also possible additionally to produce resistance printed circuit traces on diaphragm region 40 for rapid heating of the diaphragm. The background for this is faster regulation.

Again, it is possible to deposit a mirror layer on the middle diaphragm region, in order to determine the dew deposit optically.

Any micromechanical basic materials can also be used, not only the silicon substrate cited as an example.

What is claimed is:

1. A micromechanical component, comprising:
   a substrate;
   a diaphragm positioned on the substrate;
   a region arranged underneath the diaphragm and made of a porous material, the region mechanically supporting and thermally insulating the diaphragm; and
   a dew point sensor, including:
      a thermocouple for measuring a temperature and arranged above the region,
      an interdigital capacitor made of the porous material and arranged above the region,
      a Peltier element device including at least one Peltier element for heating and cooling the diaphragm, and
      a dew point measuring device for measuring a dew point with the aid of one of the following:
         a mirror for optical evaluation, and
         a capacitance of the interdigital capacitor and a temperature measured by the thermocouple.

2. The micromechanical component according to claim 1, wherein:
   the porous material is formed from a material of the substrate.

3. The micromechanical component according to claim 1, wherein:
   a hollow space is formed underneath the region.

4. The micromechanical component according to claim 1, wherein:
   the diaphragm is formed by oxidizing a surface of the substrate and a surface of the region.

5. The micromechanical component according to claim 1, wherein:
   the region is completely oxidized.

6. The micromechanical component of claim 1, wherein the micromechanical component is a micromechanical sensor.

7. The micromechanical component of claim 1, wherein the micromechanical component is a dewpoint sensor.

8. The micromechanical component of claim 1, wherein the diaphragm is a closed diaphragm.

9. A micromechanical component, comprising:
   a substrate;
   a diaphragm positioned on the substrate;
   a region arranged underneath the diaphragm and made of a porous material, the region mechanically supporting and thermally insulating the diaphragm; and
   a heat radiation sensor including:
      an absorption device for absorbing a heat radiation provided above the region,
      a Peltier element device including at least one Pelter element for generating a thermoelectric voltage corresponding to a temperature difference between a diaphragm region next to the region and a diaphragm region above the region, and
      a temperature measuring device for measuring a temperature in the diaphragm region above the region.

10. The micromechanical component according to claim 9, wherein:
    the temperature measuring device measures the temperature in the diaphragm region above the region based upon the thermoelectric voltage.

11. The micromechanical component according to claim 9, further comprising:
    a control device that operates the Peltier element device to control the temperature in the diaphragm region above the region, wherein:
       the temperature measuring device measures the temperature in the diaphragm region above the region based on a regulated output.

12. The micromechanical component of claim 9, wherein the micromechanical component is a micromechanical sensor.

13. The micromechanical component of claim 9, wherein the micromechanical component is a dewpoint sensor.

14. The micromechanical component of claim 9, wherein the diaphragm is a closed diaphragm.

15. A micromechanical component, comprising:
    a substrate;
    a diaphragm positioned on the substrate;
    a region arranged underneath the diaphragm and made of a porous material, the region mechanically supporting and thermally insulating the diaphragm; and
    a dew point sensor including:
       a thermocouple for measuring a temperature and arranged above the region,
       a capacitor made of the porous material and arranged above the region,
       a Peltier element device including at least one Peltier element for heating and cooling the diaphragm, and
       a dew point measuring device for measuring a dew point.

16. The micromechanical component according to claim 15, wherein:
    the porous material is formed from a material of the substrate.

17. The micromechanical component according to claim 15, wherein:
the diaphragm is formed by oxidizing a surface of the substrate and a surface of the region.

18. The micromechanical component according to claim 15, wherein:
a hollow space is formed underneath the region.

19. The micromechanical component according to claim 15, wherein:
the region is completely oxidized.

20. The micromechanical component according to claim 15, wherein the porous material is formed from a material of the substrate, a hollow space is formed underneath the region, the diaphragm is formed by oxidizing a surface of the substrate and a surface of the region, and the region is completely oxidized.

21. The micromechanical component of claim 15, wherein the micromechanical component is a micromechanical sensor.

22. The micromechanical component of claim 15, wherein the micromechanical component is a dewpoint sensor.

23. The micromechanical component of claim 15, wherein the diaphragm is a closed diaphragm.

24. A micromechanical component, comprising:
a substrate;
a diaphragm positioned on the substrate;
a region arranged underneath the diaphragm and made of a porous material, the region mechanically supporting and thermally insulating the diaphragm; and
a heat radiation sensor including:
an absorption device for absorbing a heat radiation provided above the region,
a Peltier element device including at least one Pelter element for generating a thermoelectric voltage corresponding to a temperature difference between a diaphragm region next to the region and a diaphragm region above the region, and
a temperature measuring device for measuring a temperature in the diaphragm region above the region;
wherein at least one of the following is provided: the porous material is formed from a material of the substrate, a hollow space is formed underneath the region, the diaphragm is formed by oxidizing a surface of the substrate and a surface of the region, and the region is completely oxidized.

25. The micromechanical component according to claim 24, wherein:
the temperature measuring device measures the temperature in the diaphragm region above the region based upon the thermoelectric voltage.

26. The micromechanical component according to claim 24, further comprising:
a control device that operates the Peltier element device to control the temperature in the diaphragm region above the region, wherein the temperature measuring device measures the temperature in the diaphragm region above the region based on a regulated output.

27. The micromechanical component of claim 24, wherein the micromechanical component is a micromechanical sensor.

28. The micromechanical component of claim 24, wherein the micromechanical component is a dewpoint sensor.

29. The micromechanical component of claim 24, wherein the diaphragm is a closed diaphragm.

* * * * *

UNITED STATES PATENT AND TRADEMARK OFFICE
CERTIFICATE OF CORRECTION

PATENT NO. : 6,832,523 B2  Page 1 of 1
DATED : December 21, 2004
INVENTOR(S) : Hubert Benzel et al.

It is certified that error appears in the above-identified patent and that said Letters Patent is hereby corrected as shown below:

Column 1,
Lines 35-36, change "using – and p-doped semiconductors" to -- using n- and p-doped semiconductors --.
Lines 41-42, change "by way of – and p-doped semiconductors areas" to -- by way of n- and p-doped semiconductors areas --.

Column 8,
Lines 1-2, change "at least one Pelter element" to -- at least one Peltier element --.

Signed and Sealed this

Sixteenth Day of August, 2005

JON W. DUDAS
*Director of the United States Patent and Trademark Office*